United States Patent
Stevenson et al.

(10) Patent No.: US 9,211,148 B2
(45) Date of Patent: Dec. 15, 2015

(54) BONE PLATE SYSTEM AND RELATED METHODS

(75) Inventors: Tara Stevenson, La Jolla, CA (US); Matthew Curran, Carlsbad, CA (US); David Schwartz, Indianapolis, IN (US); Christopher Brown, Durham, NC (US); Jody Orellana, San Diego, CA (US); Michael Brotman, San Diego, CA (US)

(73) Assignee: NuVasive, Inc., San Diego, CA (US)

(*) Notice: Subject to any disclaimer, the term of this patent is extended or adjusted under 35 U.S.C. 154(b) by 545 days.

(21) Appl. No.: 13/499,659

(22) PCT Filed: Oct. 4, 2010

(86) PCT No.: PCT/US2010/002686
§ 371 (c)(1),
(2), (4) Date: Jul. 11, 2012

(87) PCT Pub. No.: WO2011/040983
PCT Pub. Date: Apr. 7, 2011

(65) Prior Publication Data
US 2012/0271359 A1    Oct. 25, 2012

Related U.S. Application Data

(60) Provisional application No. 61/299,925, filed on Jan. 29, 2010, provisional application No. 61/248,444, filed on Oct. 3, 2009.

(51) Int. Cl.
*A61B 17/88* (2006.01)
*A61B 17/70* (2006.01)
(Continued)

(52) U.S. Cl.
CPC ........... *A61B 17/7071* (2013.01); *A61B 17/808* (2013.01); *A61B 17/8625* (2013.01)

(58) Field of Classification Search
CPC ............. A61B 17/7071; A61B 17/808; A61B 17/8625
USPC .......................................... 606/281, 282, 286
See application file for complete search history.

(56) References Cited

U.S. PATENT DOCUMENTS

2005/0131412 A1    6/2005    Olevsky et al.
2005/0251138 A1    11/2005    Boris et al.
(Continued)

FOREIGN PATENT DOCUMENTS

WO    WO-03/020143 A1    3/2003
WO    WO-03/101319 A2    12/2003
(Continued)

OTHER PUBLICATIONS

International Search Report in International Application No. PCT/US2010/002868 mailed Dec. 17, 2010, 2 pages.
(Continued)

*Primary Examiner* — Christopher Beccia
*Assistant Examiner* — Diana S Jones
(74) *Attorney, Agent, or Firm* — Jonathan Spangler; Jennifer Russell

(57) ABSTRACT

A bone plate system for use in an "open door" laminoplasty procedure, including a bone plate, a first fixation element, and at least one second fixation element. The bone plate is elongated and has a generally curved shape such that the plate has an associated radius of curvature. The plate is sized and dimensioned to span a gap between a pair of bony segments, for example a pair of bony segments constituting a divided lamina. The first and second fixation elements are each configured to securely attach the bone plate to the bony segments. The bone plate has a first end including a generally U-shaped slot extending therein such that the open end of the slot comprises a first terminal end of the plate.

7 Claims, 15 Drawing Sheets

(51) Int. Cl.
 *A61B 17/80* (2006.01)
 *A61B 17/86* (2006.01)

(56) References Cited

U.S. PATENT DOCUMENTS

2006/0064091 A1* 3/2006 Ludwig et al. .................. 606/61
2009/0177230 A1* 7/2009 Henderson et al. ........... 606/246
2009/0210012 A1 8/2009 Null et al.
2011/0106083 A1* 5/2011 Voellmicke et al. ............ 606/70
2011/0106169 A1* 5/2011 Zalenski et al. ............... 606/279

FOREIGN PATENT DOCUMENTS

WO  WO-2006/014391 A1  2/2006
WO  WO-2007/040824 A2  4/2007

OTHER PUBLICATIONS

Written Opinion of the International Searching Authority in International Application No. PCT/US2010/002686 mailed Dec. 17, 2010, 5 pages.

* cited by examiner

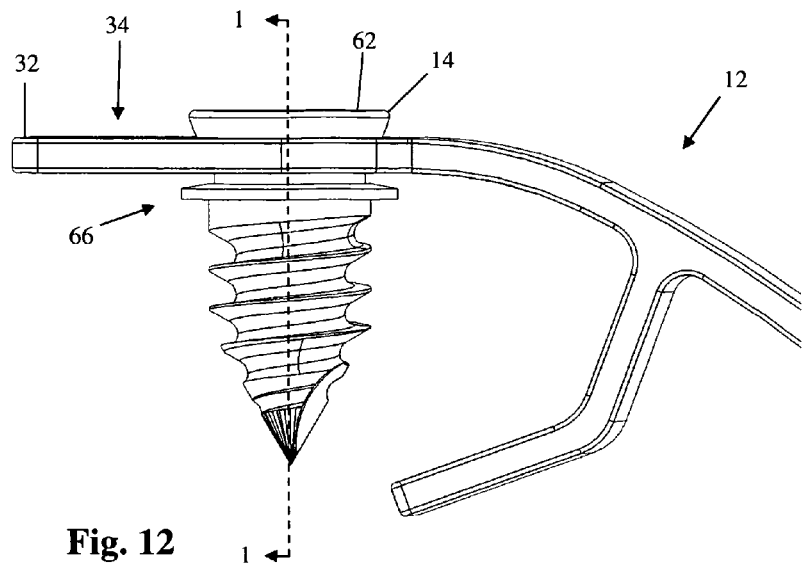
Fig. 12
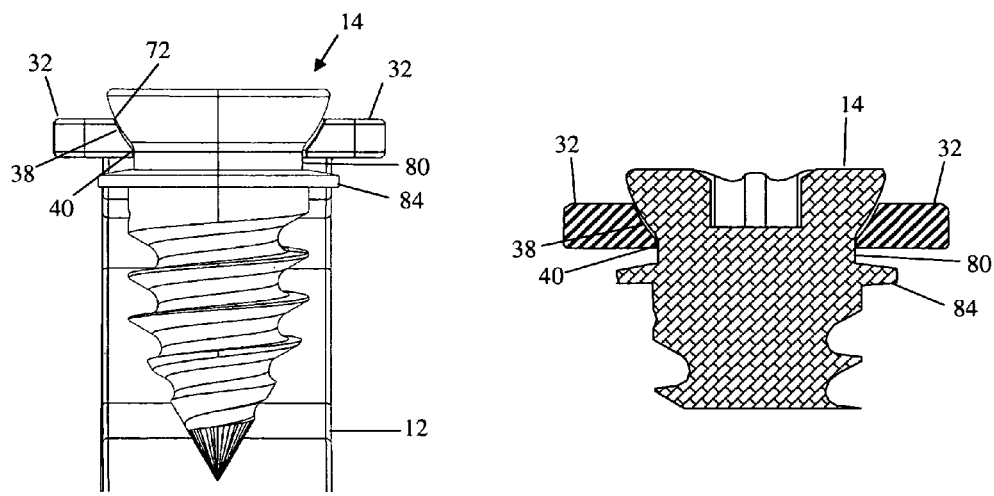
Fig. 13
Fig. 14

BONE PLATE SYSTEM AND RELATED METHODS

BACKGROUND OF THE INVENTION

I. Field of the Invention

The present invention relates to the field of laminoplasty, and, more particularly, to laminoplasty devices and methods.

II. Discussion of the Prior Art

Spinal stenosis is a degenerative narrowing of the spinal canal, nerve root canals and/or intervertebral foramina caused by bone and/or ligament hypertrophy in local, segmental or generalized regions. The narrowing results in compression of spinal nerves and nerve roots, causing a constellation of symptoms, including neck or lower back pain, neurogenic claudication and extremity pain. The leading cause of spinal stenosis is normal wear and tear on the spine, occurring in virtually the entire adult population during the natural process of aging, although spinal stenosis can occur at any age due to trauma, disease, or some medical conditions.

Surgery is currently the only treatment designed and proven to provide long term relief from spinal stenosis. One way of relieving spinal cord pressure is a surgical procedure called a laminoplasty. Laminoplasty is a surgical procedure for treating spinal stenosis (and other conditions) by relieving pressure on the spinal cord. The traditional "open door" laminoplasty procedure involves making cuts in the lamina on both sides of the spinous process of the affected vertebrae (i.e. cutting completely through the lamina on one side of the spinous process and cutting partially through the lamina on the other side of the spinous process) and then swinging the freed flap of bone open to relieve pressure on the spinal cord. For this "open door" laminoplasty procedure, one challenge is to securely maintain the grooved portion of lamina or "lamina hinge portion" for proper healing. Because the hinged side can be prone to breakage if excess pressure is applied on the lamina, the open side gutter is generally cut first, followed by the hinge side. A curved curette or nerve hook can be used to test the stability of the hinge to ensure that sufficient opening can be achieved. A graft and/or plate can then be inserted into the created opening to keep the lamina in an open position.

The existing standard open door laminoplasty technique is comprised of several steps. First, a complete cut of the lamina (called a "trough cut") is made on one side of the spinous process at the base of the lamina, where it meets the lateral mass. The bone is resected through the dorsal cortex, inner cancellous layer and ventral cortex. After this, a partial cut (called a "hinge cut") is performed on the opposite side of the spinous process, resecting the lamina where the lamina meets the lateral mass; only the dorsal cortex and inner cancellous layers are removed. A plate is then placed on the trough side spanning a gap between the severed lamina and the lateral mass, and the lateral mass screws are inserted through one end of the plate and into the lateral mass. Finally, the laminar screw is inserted through the other end of the plate and into the lamina.

This traditional procedure can be risky to perform largely because the cuts in the lamina are made before the hole for the laminar screw are drilled. This means that the surgeon is likely drilling through an unstable lamina directly over otherwise exposed spinal cord. The present invention is directed at overcoming, or at least improving upon, the disadvantages of the prior art.

SUMMARY OF THE INVENTION

The present invention describes a bone plate system for use in an open door laminoplasty procedure. The laminoplasty fixation system of the present invention increases the safety and reproducibility of the procedure by eradicating the steps of drilling and screwing over an open spinal cord and an unstable hinged lamina. The open U-shaped plate design of the present invention facilitates the placement of the laminar screw before cuts are made to the laminae, eliminating the risks of drilling and/or screwing over an open cord and hinged lamina.

The steps of the present invention comprise placement of the laminar screw prior to cutting the laminae. After placement of the laminar screw, a trough cut is made on one side of the spinous process at the base of the lamina, where it meets the lateral mass. The bone is resected through the dorsal cortex, inner cancellous layer and ventral cortex. After this, the hinge cut is performed, resecting the lamina (on the opposite side of the spinous process) where the lamina meets the lateral mass; only the dorsal cortex and inner cancellous layer are removed. A plate is then engaged with the laminar screw on the trough side and the lamina is "lifted" (e.g. pivoted about the hinge cut) to create a gap between the lateral mass and the lamina. The plate is positioned such that it spans the gap and a portion is positioned over the lateral mass. The lateral mass screws are then inserted to secure the plate.

By way of example only, the bone plate system includes a bone plate, a first fixation element, and at least one second fixation element. The bone plate is elongated and has a generally curved shape such that the plate has an associated radius of curvature. The plate is sized and dimensioned to span a gap between a pair of bony segments, for example a pair of bony segments constituting a divided lamina. The first and second fixation elements are each configured to securely attach the bone plate to the bony segments.

The bone plate includes a first end, a second end, and a body portion extending therebetween. The first end comprises a pair of first flanges that extend from the body portion and in effect are a continuation of the body portion (as opposed to extending away from the body portion at a particular angle). Unlike the body portion, however, the first flanges are generally planar. The first flanges define the sides of a slot that is dimensioned to engage the first fixation element. The slot is a generally U-shaped slot with its open end constituting one terminal end of the bone plate.

The second end of the bone plate comprises a second flange extending from the body portion. The second flange forms an acute angle with the body portion. The second flange includes a pair of apertures extending through the second flange from the first surface to the second surface. The apertures are each dimensioned to receive one of the second fixation elements. Although shown as having a pair of apertures, any number of apertures may be provided without departing from the scope of the present invention.

The body portion is a generally elongated element that extends between the first end and second end of the bone plate. The body portion includes a third flange extending away from the second surface. The third flange includes a first portion and a second portion. The first portion extends between the body portion of the bone plate and the second portion of the third flange. The second portion extends away from the first portion in a direction generally toward the first end of the bone plate. The second portion further forms an obtuse angle with the first portion. The junction between the first portion and the body portion of the bone plate forms a first crotch that is configured for abutment against a first bony segment. At the second end of the bone plate, the body portion includes a second terminal end that extends beyond the junction of the second flange. The junction between the second terminal end and the second flange forms a second crotch that is configured for abutment against a second bony segment. The second terminal end includes a generally planar abutment surface that faces the direction of the second flange.

By way of example only, the first fixation element comprises a bone screw having a head, a shank, and a neck. The head includes a top surface having a central aperture formed therein for engagement with an insertion tool (not shown). The central aperture may be provided in any shape corresponding to the shape of the engagement member of the insertion tool. The head further includes an annular convex outer surface that is generally oriented toward the shank and extends between the top surface and the neck. The shank includes a threadform, a distal tip, and a recess, which each cooperate to provide a self-tapping bone screw capable of providing sufficient purchase within bone to secure the bone plate in position.

The neck includes a first portion, a second portion, and an annular ledge that is positioned between the first portion and second portion. The first and second portions are sized such that the second portion has a greater diameter than the first portion. The annular ledge has a diameter that is greater than the diameters of the first and second portions, and also greater than the major diameter of the head. This is to prevent backout of the first fixation element after insertion into bone. The annular ledge has a first surface oriented toward the head and a second surface oriented toward the shank. The first surface may be provided as a convex or otherwise tapered surface to enable slight angular adjustment of the first fixation element relative to the base plate. The second surface is generally planar and is adapted to interface with the bony segment, however other configurations are possible without departing from the scope of the present invention.

When mated with the bone plate, the first fixation element is seated within the slot of the bone plate. The ledge of the first fixation element is then positioned underneath the first flanges, such that the ledge would come in contact with the flanges if the first fixation element should try to back out of the bone.

A template tool can be used to help mark a lamina, as an alternative to or in addition to using a bone plate, for placement of a laminar screw. The template tool includes a handle, rod and distal end. The handle provides grip and control of the template tool. The rod can be straight, curved, and/or bent in one or more locations, so as to provide sufficient vertical and/or horizontal displacement of the handle and rod portion from the surgical site during use to enable adequate visualization of the operative site during use. The distal end of the template tool includes an attachment which is shaped similarly to a first end of a bone plate to be used during the laminoplasty procedure. The attachment can be permanently fixed to the rod, or alternatively, removably attached so as to make the attachment interchangeable with various attachments. The attachment allows proper marking of a laminar screw site prior to use of the bone plate being used for fixation. The template tool provides increased visibility of the surgical site, allowing a surgeon to mark the laminar screw site while visibility is optimized, rather than when visibility may be obstructed, as during placement of the bone plate against the surgical site by hand.

The base of the attachment includes side segments extending laterally from base of the attachment. The side segments act as a guide, providing proper positioning of the U-shaped end of the attachment, by lining up where the lateral mass meets the lamina. The side segments are lined up before the surgeon marks the area for placing a laminar screw. The attachment can extend straight and perpendicularly from the distal end where the rod and attachment meet, or curved or bent, to accommodate the contours of the surgical site, while still allowing optimized visibility of the surgical site depending on the configuration of the handle and rod assembly.

In use, the laminoplasty fixation system described herein allows for an increase in safety and reproducibility over the traditional laminoplasty surgical technique. According to the novel technique described herein, after a standard C2 to T1 midline posterior exposure and visualization of the lateral masses, a first fixation element (e.g. "laminar screw") can be placed in each lamina to which a bone plate is being applied. The first fixation elements should be placed at the midpoint of the lamina between the lateral mass and the curvature where the spinous process begins. This location can be determined by using a template tool described herein. The open side trough can then be cut completely through the lamina on the same side of the spinous process as the first fixation element. The hinge cut is then formed on the opposite side of the spinous process. The stability of the hinge should be tested to ensure that sufficient opening can be achieved and to evaluate the size of plate necessary for decompression. A bone plate of the appropriate size is then selected (and the corresponding graft, if being used, can be attached to the plate) and the plate can then be inserted by sliding the U-shaped slot of the plate under the head of the previously placed first fixation element. The plate is thus positioned such that the pair of first flanges is adjacent a first surface of the divided lamina. The first portion of the third flange is positioned adjacent to and potentially abuts the cut end of the divided lamina, and the second portion of the third flange is positioned adjacent to and potentially abuts at least a portion of a second surface of the divided lamina. Thus, the first crotch is generally in contact with the cut end of the lamina. The plate may then be used to lift the lamina until the second terminal end of the body portion of the plate contacts the cut edge of the lateral mass. Alternatively, the lamina can be lifted and held in an open position with a secondary instrument, for example a curette or a nerve hook, while the plate is engaged with the first fixation element. The plate is positioned such that the second crotch rests against the cut edge of the lateral mass, and the second flange is positioned adjacent the lateral mass. Once the bone plate is properly positioned against the lateral mass, the second fixation element(s) can be inserted through aperture(s) and into the lateral mass bone. At this point the lamina is securely propped open. The surgical incision can be closed, completing the procedure. Any number of bone plates can be inserted on any number of lamina without departing from the scope of the present invention.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein:

FIGS. 12-13 are side and end plan views, respectively, of a first end of the bone plate of FIG. 3 engaged with a first bone anchor of FIG. 8;

FIG. 14 is a cross-sectional view of the first end of bone plate and anchor combination of FIG. 13;

DETAILED DESCRIPTION OF THE PREFERRED EMBODIMENT

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The bone plate system disclosed herein boasts a variety of inventive features and components that warrant patent protection, both individually and in combination.

As described herein by way of example only, the spinal implant disclosed herein is used in an "open door" laminoplasty procedure. Each of the embodiments described herein are shown as illustrative examples of the inventive concept, and any features described with respect to a particular embodiment are not to be construed as limited to that particular embodiment, but rather may be used in combination with any features of any embodiment described herein without departing from the scope of the present invention.

Figure 1:
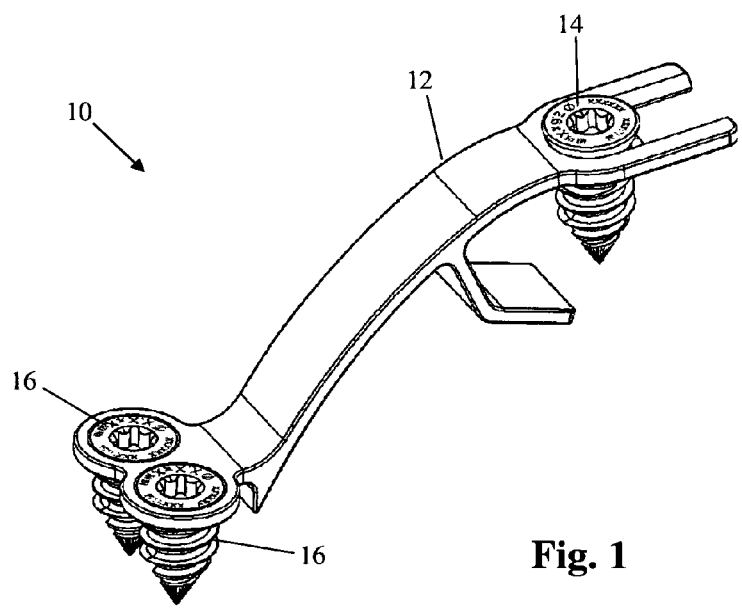
FIG. 1 is a perspective view of an example of a bone plate system configured for use during an open door laminoplasty procedure, according to a first embodiment of the present invention.
Figure 2:
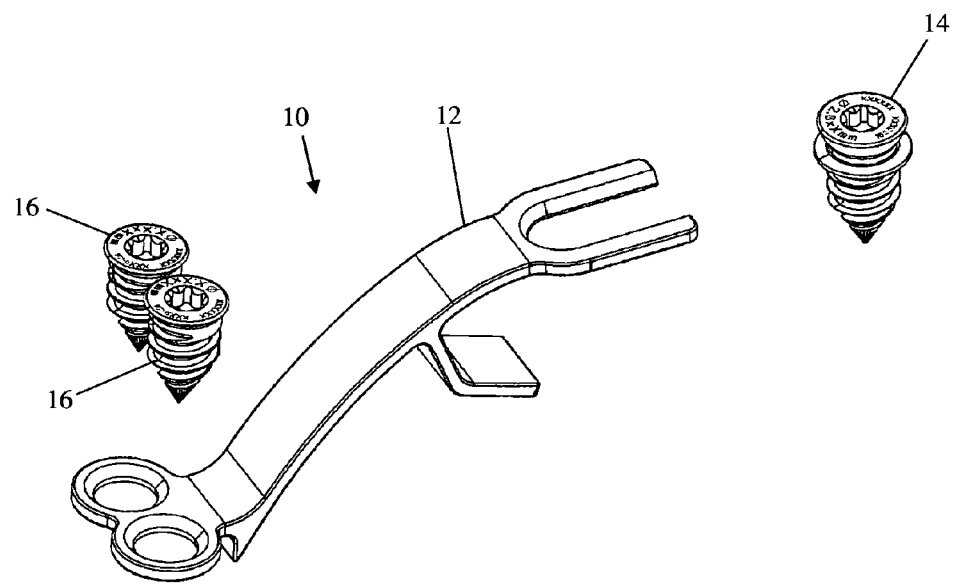
FIG. 2 is an exploded perspective view of the bone plate system of FIG. 1.
Figure 3:
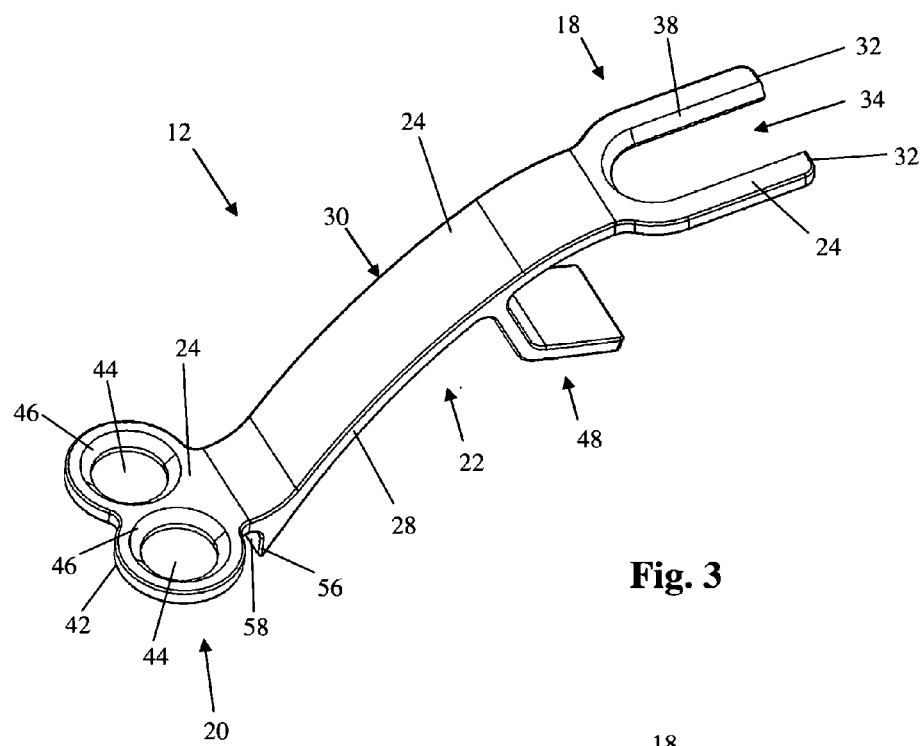
FIGS. 3-4 are perspective views of a bone plate forming part of the bone plate system of FIG. 1.
Figure 4:
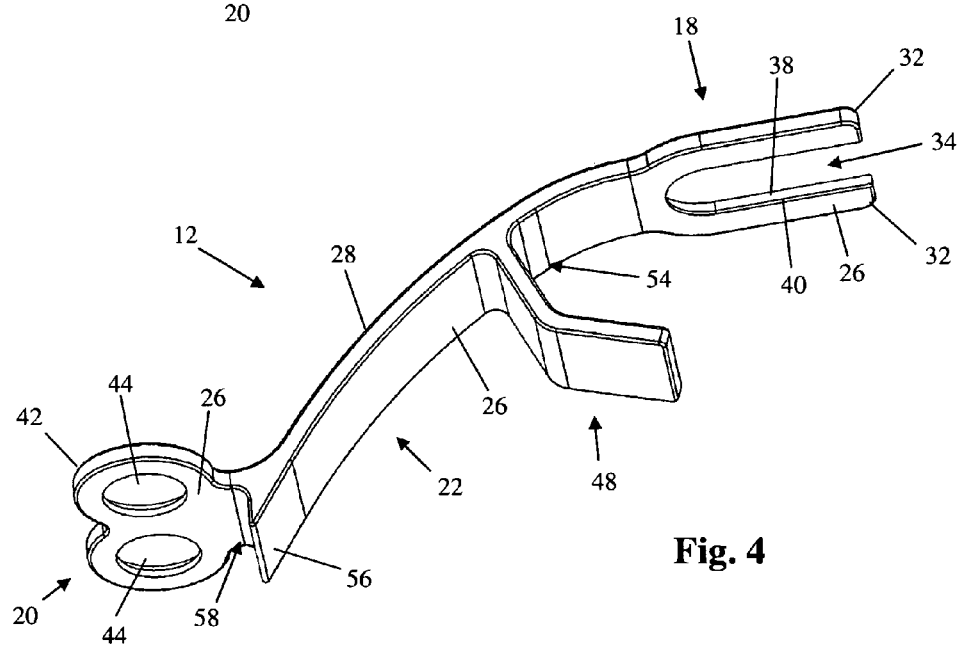
Figure 5:
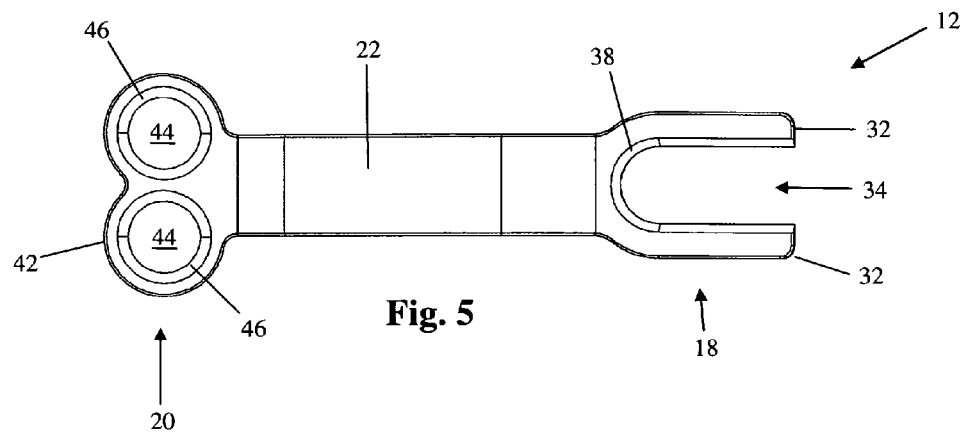
FIGS. 5-6 are top and side plan views, respectively, of the bone plate of FIG. 3.
Figure 6:
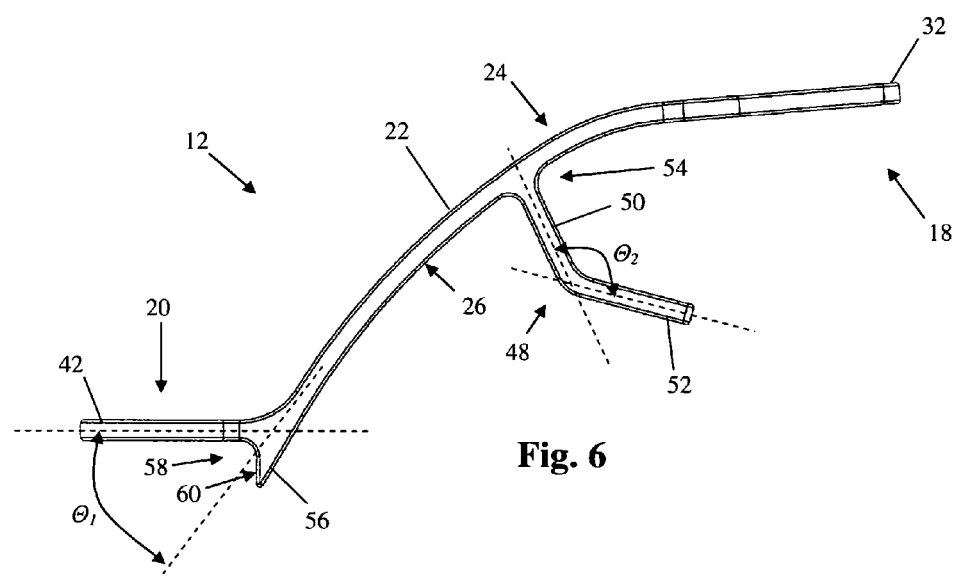

FIGS. 1-2 illustrate an example of a bone plate system 10 configured for use in a laminoplasty procedure, according to a first embodiment of the present invention. By way of example only, the bone plate system 10 includes a bone plate 12, a first fixation element 14, and at least one second fixation element 16. The bone plate 12 is elongated and has a generally curved shape such that the plate 12 has an associated radius of curvature. The plate is sized and dimensioned to span a gap between a pair of bony segments, for example a pair of bony segments constituting a divided lamina. The first and second fixation elements 14, 16 are each configured to securely attach the bone plate 12 to the bony segments. Although shown by way of example in FIGS. 1 and 2 as being bone screws, other fixation elements are possible without departing from the scope of the present invention, for example tacks, nails, hooks, pins, sutures, adhesives, and the like.

The bone plate 12, first fixation element 14, and second fixation element 16 may be manufactured from any suitable material without departing from the scope of the present invention, including but not limited to metal (e.g. titanium), polymer (e.g. poly-ether-ether-ketone), ceramic, and the like.

Figure 7:
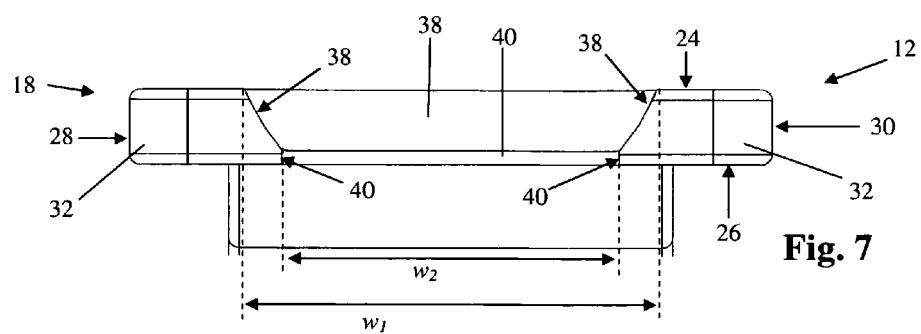
FIG. 7 is a plan view of a first end of the bone plate of FIG. 3.

Referring to FIGS. 3-7, the bone plate 12 is described in further detail. The bone plate 12 includes a first end 18, a second end 20, and a body portion 22 extending therebetween. The bone plate 12 further includes a first surface 24, second surface 26, and two lateral surfaces 28, 30 that form the perimeter of the bone plate 12. The first end 18 comprises a pair of first flanges 32 that extend from the body portion 22, and in effect are a continuation of the body portion 22 (as opposed to extending away from the body portion 22 at a particular angle). Unlike the body portion 22, however, the first flanges 32 are generally planar. The first flanges 32 define the sides of a slot 34 that is dimensioned to engage the first fixation element 14, as will be described in further detail below. The slot 34 is a generally U-shaped slot with its open end constituting a first terminal end of the bone plate 12. The inside edges of the generally U-shaped slot 34 are defined by a concave surface 38 and a planar surface 40, as best shown in FIG. 7. The concave surface 38 intersects the first surface 24 of the bone plate 12 and is dimensioned to engage the head 62 of the first fixation element 14 such that the head 62 is seated within the concave surface 38 while in use. The other end of the concave surface 38 intersects the planar surface 40 which in turn extends between the concave surface 38 and the second surface 26 of the bone plate 12. The planar surface 40 is generally perpendicular to the second surface 26 at the first end 18. Thus, the width $w_1$ of the slot 34 in the plane of the first surface 24 of the bone plate 12 is greater than the width $w_2$ of the slot 34 in the plane of the second surface 26 of the bone plate 12.

The second end 20 of the bone plate 12 comprises a second flange 42 extending from the body portion 22. The second flange 42 forms an acute angle $\Theta_1$ with the body portion 22. The second flange 42 includes a pair of apertures 44 extending through the second flange 42 from the first surface 24 to the second surface 26. The apertures 44 are each dimensioned to receive one of the second fixation elements 16. Although shown as having a pair of apertures 44, any number of apertures 44 may be provided without departing from the scope of the present invention. As shown by way of example, the apertures 44 are offset from the longitudinal midline of the bone plate 12, and are arranged such that a line extending through the centers of the apertures 44 is transverse to the longitudinal midline of the bone plate 12. However, other arrangements are possible. For example, the apertures 44 could be provided in a linear arrangement in line with the longitudinal midline of the bone plate 12. Alternatively, the offset apertures 44 could be arranged such that a line connecting the centers thereof is not normal to the longitudinal axis of the bone plate 12. Each aperture 44 includes a concave surface 46 adjacent to the first surface 24. The concave surface 46 is dimensioned to engage the head 90 of the second fixation element 16 such that the head 90 is seated within the concave surface 46 while in use.

The body portion 22 is a generally elongated element that extends between the first end 18 and second end 20 of the bone plate 12. The body portion 22 includes a third flange 48 extending away from the second surface 26. The third flange 48 includes a first portion 50 and a second portion 52. The first portion 50 extends between the body portion 22 of the bone plate 12 and the second portion 52 of the third flange 48. The second portion 52 extends away from the first portion 50 in a direction generally toward the first end 18 of the bone plate 12. The second portion 52 further forms an obtuse angle $\Theta_2$ with the first portion 50. The junction between the first portion 50 and the body portion 22 of the bone plate forms a first crotch 54 that is configured for abutment against a first bony segment. At the second end 20 of the bone plate, the body portion 22 includes a terminal end 56 that extends beyond the junction of the second flange 42. The junction between the terminal end 56 and the second flange 42 forms a second crotch 58 that is configured for abutment against a second bony segment. The terminal end 56 includes a generally planar abutment surface 60 that faces the direction of the second flange 42.

Figure 8:
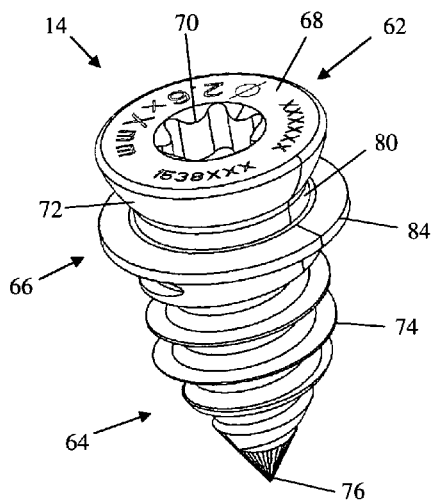
FIGS. 8-9 are perspective and plan views, respectively, of a first bone anchor forming part of the bone plate system of FIG. 1.
Figure 9:
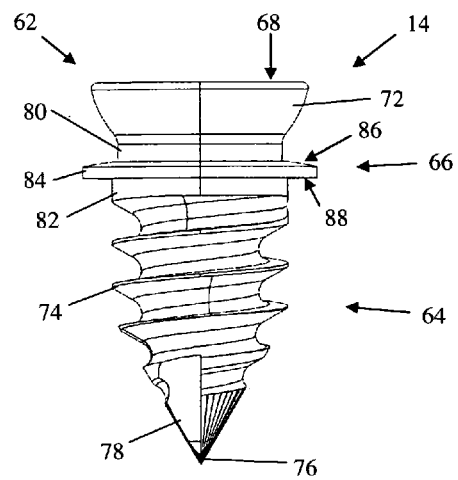

FIGS. 8-9 illustrate an example of a first fixation element 14 forming part of the bone plate system 10 according to one embodiment of the present invention. By way of example only, the first fixation element 14 comprises a bone screw having a head 62, a shank 64, and a neck 66. As will be explained below, the first fixation element 14 of the present example is configured for placement in the lamina, and may therefore be used interchangeably with the term "laminar screw 14." The head 62 includes a top surface 68 having a central aperture 70 formed therein for engagement with an insertion tool (not shown). The central aperture 70 may be provided in any shape corresponding to the shape of the engagement member of the insertion tool. The head 62 further includes an annular convex outer surface 72 that is generally oriented toward the shank 64 and extends between the top surface 68 and the neck 66. The convex outer surface 72 is dimensioned to be received within the concave surface 38 of the first end 18, described above. The shank 64 includes a threadform 74, a distal tip 76, and a recess 78, which each cooperate to provide a self-tapping bone screw capable of providing sufficient purchase within bone to secure the bone plate 12 in position.

The neck 66 includes a first portion 80, a second portion 82, and an annular ledge 84 that is positioned between the first portion 80 and second portion 82. The first and second portions 80, 82 are sized such that the second portion 82 has a greater diameter than the first portion 80. The annular ledge 84 has a diameter that is greater than the diameters of the first and second portions 80, 82, and also greater than the major diameter of the head 62. This is to prevent backout of the first fixation element 14 after insertion into bone. The annular ledge 84 has a first surface 86 oriented toward the head 62 and a second surface 88 oriented toward the shank 64. The first surface 62 may be provided as a convex or otherwise tapered surface to enable slight angular adjustment of the first fixation element 14 relative to the base plate 12. The second surface 88 is generally planar and is adapted to interface with the bony segment, however other configurations are possible without departing from the scope of the present invention.

Although shown by way of example as a laminar screw 14 with an annular ledge 84, other embodiments of the first fixation element 14 are possible. For example, the first fixation element 14 may comprise a nut and bolt combination without departing from the scope of the present invention. The use of a nut and bolt combination may allow for alternative embodiments of the bone plate 12, for example a bone plate including a first end with enclosed apertures (instead of the U-shaped slot shown and described by example herein).

Figure 10:
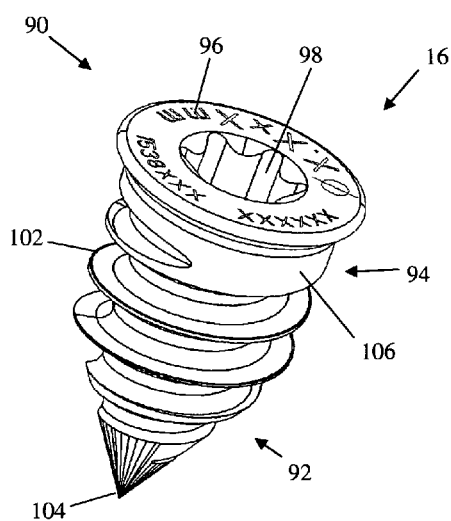
FIGS. 10-11 are perspective and plan views, respectively, of a second bone anchor forming part of the bone plate system of FIG. 1.
Figure 11:
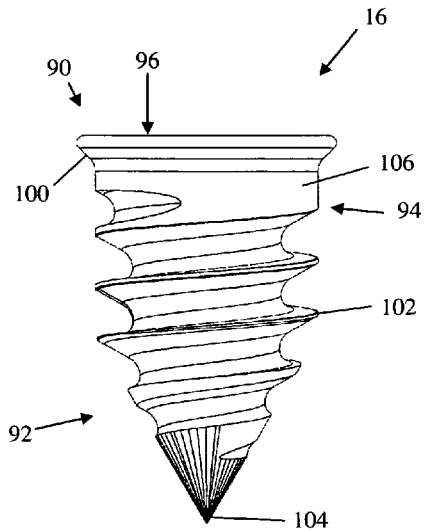

FIGS. 10-11 illustrate an example of a second fixation element 16 forming part of the bone plate system 10 according to one embodiment of the present invention. By way of example only, the second fixation element 16 comprises a bone screw having a head 90, a shank 92, and a neck 94. The head 90 includes a top surface 96 having a central aperture 98 formed therein for engagement with an insertion tool (not shown). The central aperture 98 may be provided in any shape corresponding to the shape of the engagement member of the insertion tool. The head 90 further includes an annular convex outer surface 100 that is generally oriented toward the shank 92 and extends between the top surface 96 and the neck 94. The convex outer surface 100 is dimensioned to be received within the concave surface 46 of the aperture(s) 44 of the second end 20, described above. The shank 92 includes a threadform 102 and a distal tip 104, which each cooperate to provide a self-tapping bone screw capable of providing sufficient purchase within bone to secure the bone plate 12 in position. The neck 94 includes a generally cylindrical surface 106 of a uniform diameter.

FIGS. 12-14 illustrate the first end 18 of the bone plate 12 when mated with the first fixation element 14. The first fixation element 14 sits within the slot 34 of the bone plate 12 such that the convex outer surface 72 of the head 62 of the first fixation element 14 is seated within the concave surface 38 that forms part of the periphery of the slot 34. The planar surface 40 abuts against the first portion 80 of the neck 66 of the first fixation element 14. The ledge 84 is then positioned underneath the first flanges 32, such that the ledge 84 would come in contact with the flanges 32 if the first fixation element 14 should try to back out of the bone.

Figure 15:
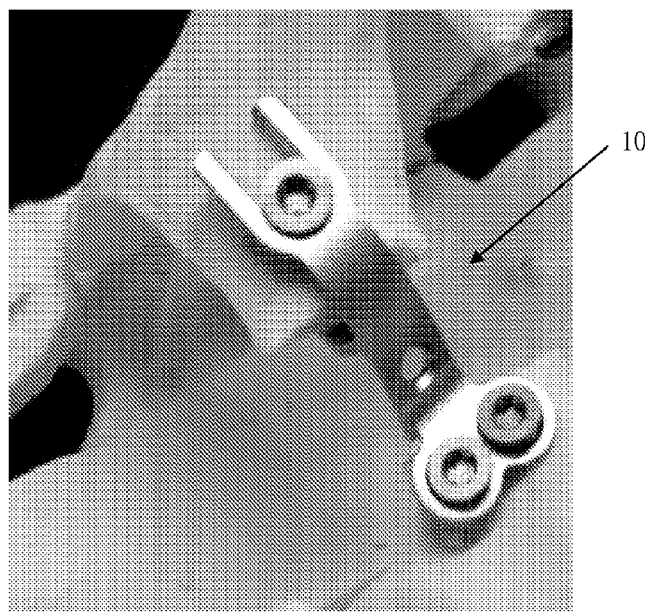
FIG. 15 is a plan view of a bone plate system of FIG. 1 engaged with bone.
Figure 16:
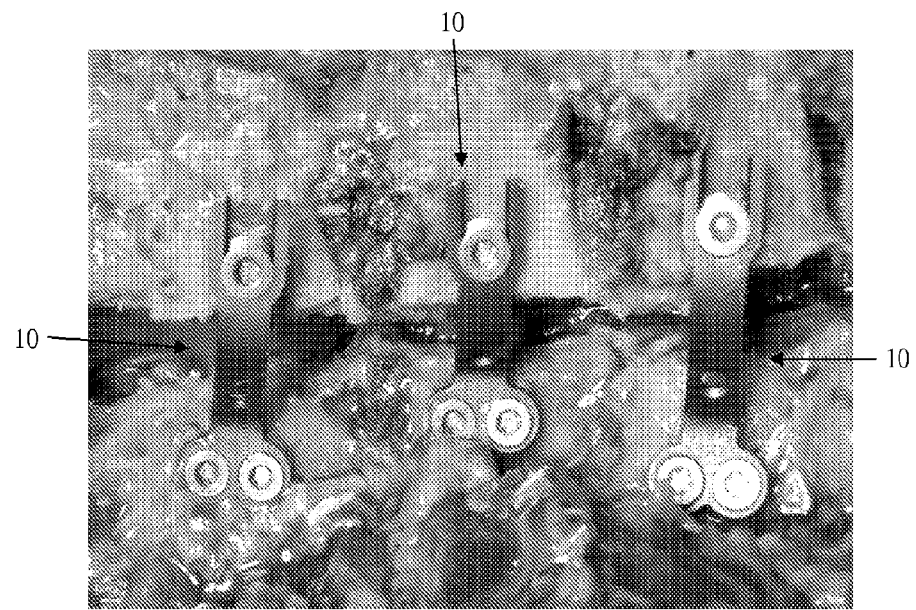
FIG. 16 is a plan view of a plurality of bone plate systems of FIG. 1 engaged with bone.

FIGS. 15-16 illustrate bone plate system 10 affixed to the lamina and lateral mass, in a single and multiple, respectively, laminoplasty fixation system configuration.

The bone plate system 10 is suitable for use in a laminoplasty procedure. In such a procedure, the first step is to establish an operative corridor within a patient to a surgical target site. After a standard C2 to T1 midline posterior exposure and visualization of the lateral masses, a first fixation element 14 can be placed in each lamina to which a bone plate 12 is being applied. The first fixation elements 14 should be placed at the midpoint of the lamina between the lateral mass and the curvature where the spinous process begins. Proper placement of the first fixation element 14 may be determined with the use of a template tool 600, described by way of example below. The open side trough can then be cut completely through the lamina on the same side of the spinous process as the first fixation element 14. The hinge cut is then made in the lamina on the opposite side of the spinous process. The stability of the hinge should be tested to ensure that sufficient opening can be achieved and to evaluate the size of plate necessary for decompression. A bone plate 12 of the appropriate size is then selected and a corresponding bone graft, if being used, can be attached to the plate. The bone plate 12 can then be inserted by sliding the U-shaped slot 34 of the plate 12 under the head 62 of the previously placed first fixation element 14. The plate 12 is thus positioned such that the pair of first flanges 32 is adjacent with a first surface of the divided lamina. The first portion 50 of the third flange 48 is positioned adjacent to and potentially abuts the cut end of the divided lamina, and the second portion 52 of the third flange 48 is positioned to and potentially abuts at least a portion of a second surface of the divided lamina. Thus, the first crotch 54 is generally in contact with the cut end of the lamina. The plate 12 may then be used to lift the lamina until the second terminal end 56 of the body portion 22 of the plate 12 contacts the cut edge of the lateral mass. Alternatively, the lamina can be lifted and held in an open position with a secondary instrument, for example a curette or a nerve hook while the plate is engaged with the first fixation element 14. The plate 12 is positioned such that the second crotch 58 rests against the cut edge of the lateral mass, and the second flange 42 is positioned adjacent the lateral mass. Once the bone plate 12 is properly positioned against the lateral mass, the second fixation elements 16 can be inserted through apertures 44 and into the lateral mass bone. At this point the lamina is securely propped open. The surgical incision can be closed, completing the procedure. Any number of bone plates 12 can be inserted on any number of lamina without departing from the scope of the present invention.

According to one example of the present invention, the bone plate 12 may be inserted into the surgical target site at an oblique angle relative to the lamina. The bone plate 12 is engaged with the first fixation element 14 as described herein. As the lamina is being lifted, the bone plate 12 may then be rotated into position such that the second end 20 is adjacent the lateral mass.

Figure 17:
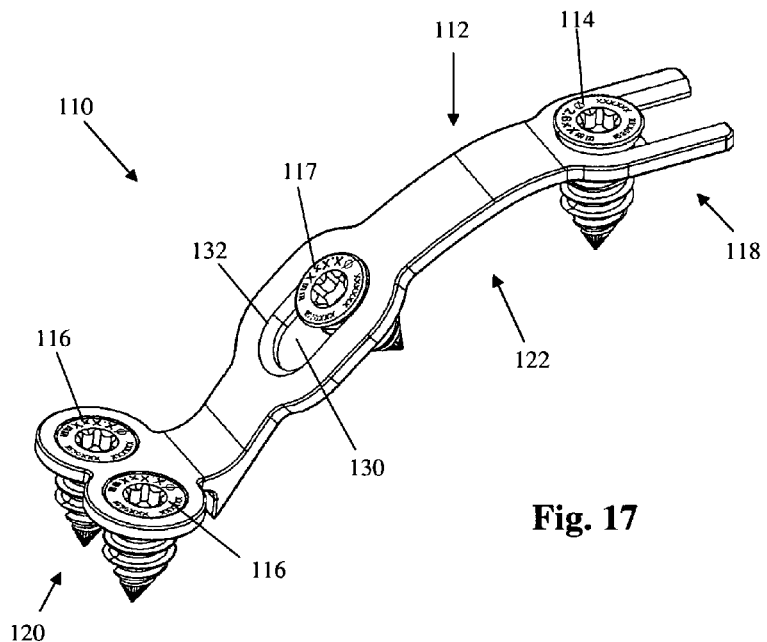
FIG. 17 is a perspective view of a bone plate system configured for use during an open door laminoplasty procedure, according to a second embodiment of the present invention.
Figure 32:
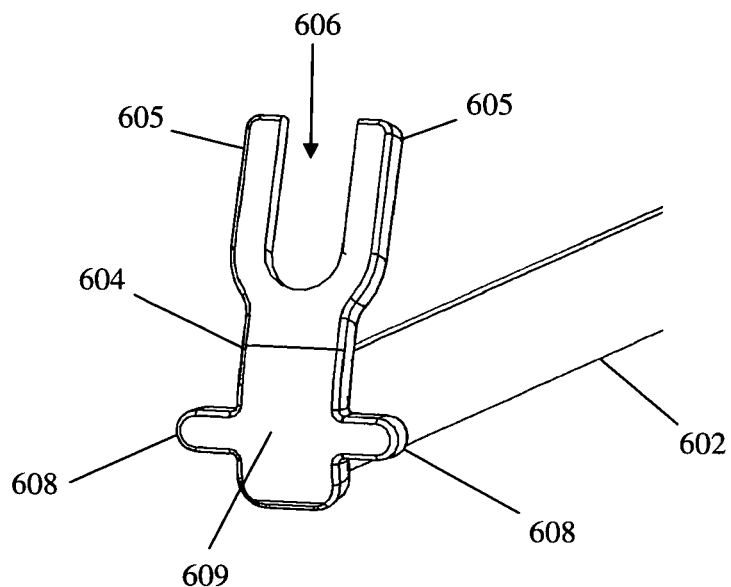
FIG. 32 is a perspective bottom view of a distal end of the template tool of FIG. 30.

Referring to FIG. 17, an example of a bone plate system 110 is provided according to a second embodiment of the present invention. The bone plate system 110 is similar to the bone plate system 10 described above except that the bone plate system 110 is configured to be used with a bone graft, for example the bone graft 700 shown in FIG. 32. By way of example only, the bone plate system 110 includes a bone plate 112, a first fixation element 114, at least one second fixation element 116, and a third fixation element 117. The bone plate 112 is elongated and has a generally curved shape such that the plate 112 has an associated radius of curvature. The plate 112 is sized and dimensioned to span a gap between a pair of bony segments, for example a pair of bony segments constituting a divided lamina. The first and second fixation elements 114, 116 are each configured to securely attach the bone plate 112 to the bony segments. The third fixation element 117 is configured to securely attach a bone graft, for example, the bone graft 700 shown in FIG. 32 to the bone plate 112. Although shown by way of example in FIG. 17 as being bone screws, other fixation elements are possible without departing from the scope of the present invention, for example nuts and bolts, tacks, nails, hooks, pins, sutures, adhesives, and the like.

The bone plate 112 includes a first end 118, a second end 120, and a body portion 122 extending therebetween. The first and second ends 118, 120, of the bone plate 112 are identical in form and function to the first and second ends 18, 20, of the bone plate system 10 described above, rendering a repeat discussion unnecessary. It is to be understood that the features described above with respect to the first and second ends 18, 20 of bone plate 12 also apply to the first and second ends 118, 120 of the bone plate 112. The body portion 122 is a generally elongated element that extends between the first end 118 and second end 120 of the bone plate 112. The body portion 122 includes an elongated aperture 130 formed through the body portion 122. The aperture 130 is dimensioned to receive the third fixation element 117 therethrough. The aperture 130 includes a concave inner surface 132 for interacting with the head of the third fixation element 117.

In use, the procedure involved with the bone plate system 110 is identical to that for the bone plate system 10 except for the added step of securing a bone graft to the bone plate system 110 using the third fixation element 117. This step occurs prior to engaging the slot of the plate with the first fixation element. The bone graft may be of any size sufficient to fill the gap between the cut edge of the lamina and the cut edge of the lateral mass. Over time, the bone graft will reform a bony bridge between the lamina and lateral mass. Additional bone growth enhancers, such as bone morphogenic protein, calcium hydroxyapatite, stem cell material, collagen based bone substitute, and/or synthetic bone substitute may be used without departing from the scope of the present invention. Alternatively, a spacer made of non-bone material may be used without departing from the scope of the present invention.

Figure 18:
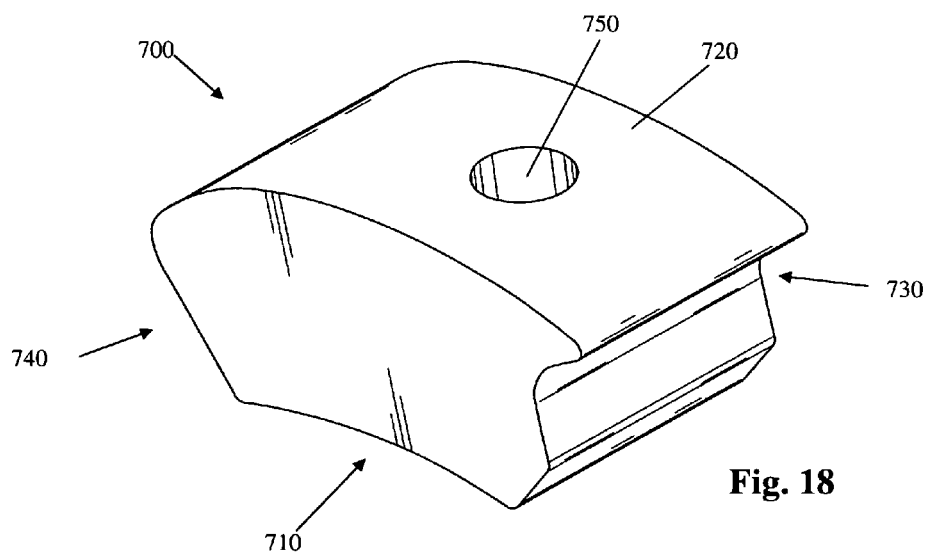
FIG. 18 is a perspective view of a bone graft configured for use with a laminoplasty fixation system according to the present invention.
Figure 19:
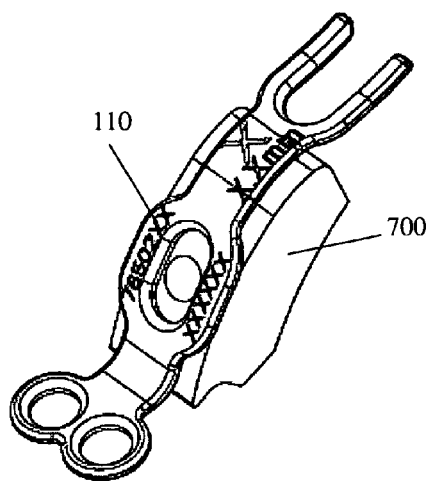
FIGS. 19-20 are perspective and side views, respectively, of the bone graft of FIG. 18 as used with the plate system of FIG. 17 according to the present invention.
Figure 20:
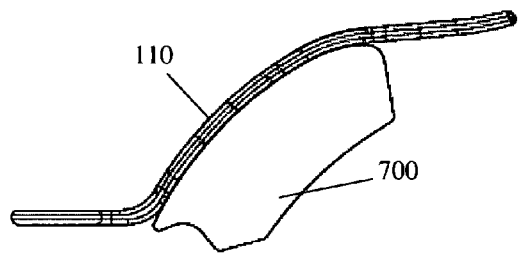

FIG. 18 illustrates an exemplary embodiment of a bone graft 700 according to the present invention. By way of example only, the bone graft 700 is an allograft constructed of solid cortical bone. The bone graft 700 has a bottom surface 710, a top surface 720, a first end 730 and a second end 740. The bottom surface 710 of the bone graft 700 comprises a concave surface, such that the bone graft 700 is anatomically shaped to maximize cord space in an axial plane. The top surface 720 of the bone graft 700 has a generally curved shape, such that the radius of curvature matches the radius of curvature of the body portion 122 of the bone plate 112, as shown in FIGS. 19-20. According to the exemplary embodiment shown in FIG. 18, the bone graft 700 has an aperture 750 extending from the top surface 720 to the bottom surface 710. The aperture 750 is dimensioned to align with the elongated aperture 130 of the bone plate 112 and to receive the third fixation element 117 therethrough. The first end 730 of the bone graft 700 is generally V-shaped, forming a crotch that is configured for abutment against a bony segment, such as a lateral mass. The second end 740 of the bone graft 700 is dimensioned to maximize contact between the second end 740 and a bony segment. By way of example only, the angle of the second end 740 of the bone graft 700 complements the angle of the end of the divided lamina cut according to the laminoplasty procedure of the present invention.

Figure 21:
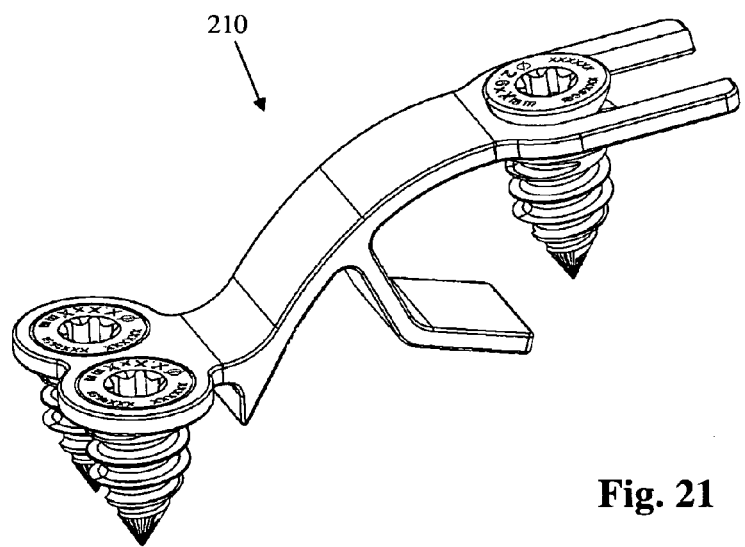
FIG. 21 is a perspective view of a bone plate system configured for use during an open door laminoplasty procedure, according to a third embodiment of the present invention.

FIG. 21 illustrates a bone plate system 210 according to a third embodiment of the present invention. The bone plate system 210 is identical to the bone plate system 10 except that it is provided with a smaller size. Many different sizes of the bone plate system 10/210 may be provided without departing from the scope of the present invention.

Figure 22:
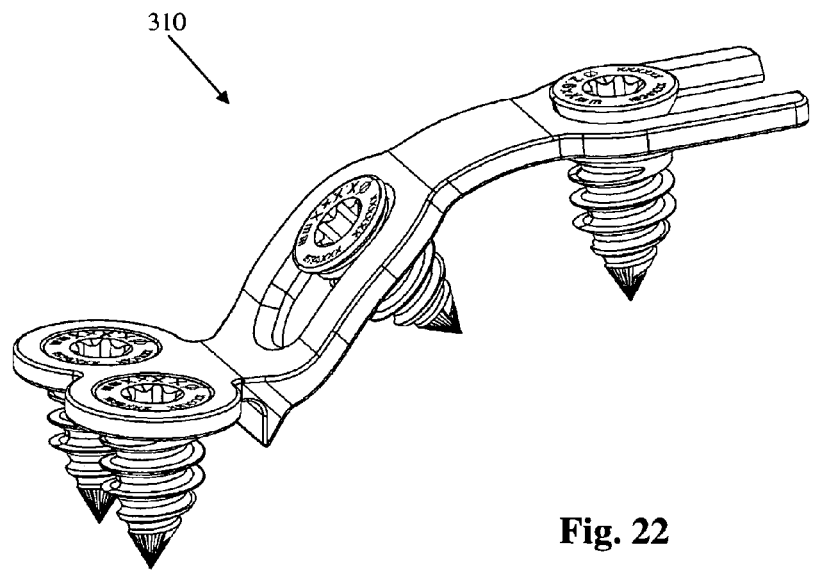
FIG. 22 is a perspective view of a bone plate system configured for use during an open door laminoplasty procedure, according to a fourth embodiment of the present invention.
Figure 23:
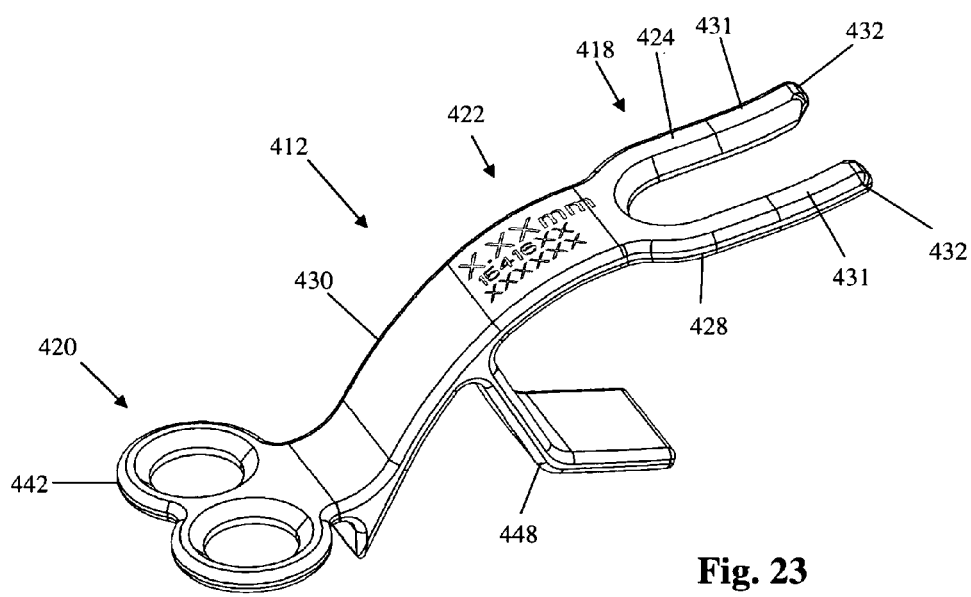
FIG. 23 is a perspective view of a bone plate forming part of a bone plate system configured for use during an open door laminoplasty procedure, according to a fifth embodiment of the present invention.
Figure 24:
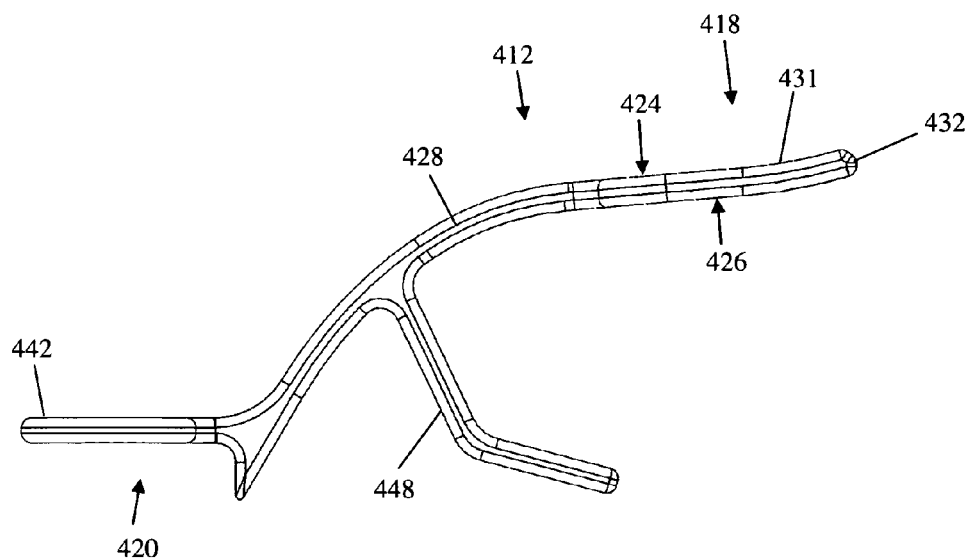
FIG. 24 is a side plan view of the bone plate of FIG. 23.
Figure 25:
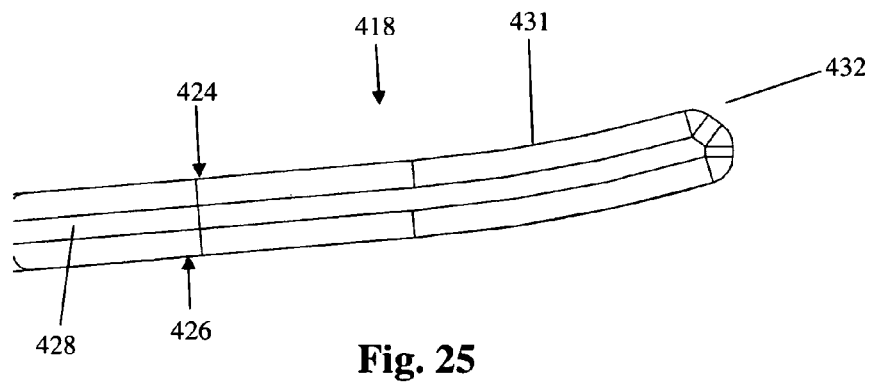
FIG. 25 is a side plan view of a first end of the bone plate of FIG. 23.
Figure 26:
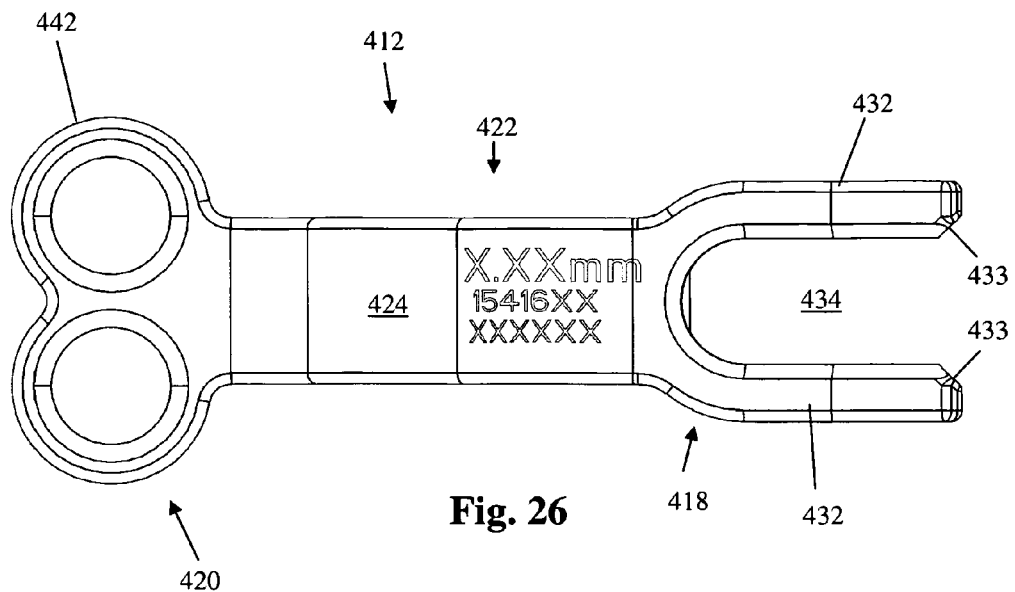
FIG. 26 is a top plan view of the bone plate of FIG. 23.
Figure 27:
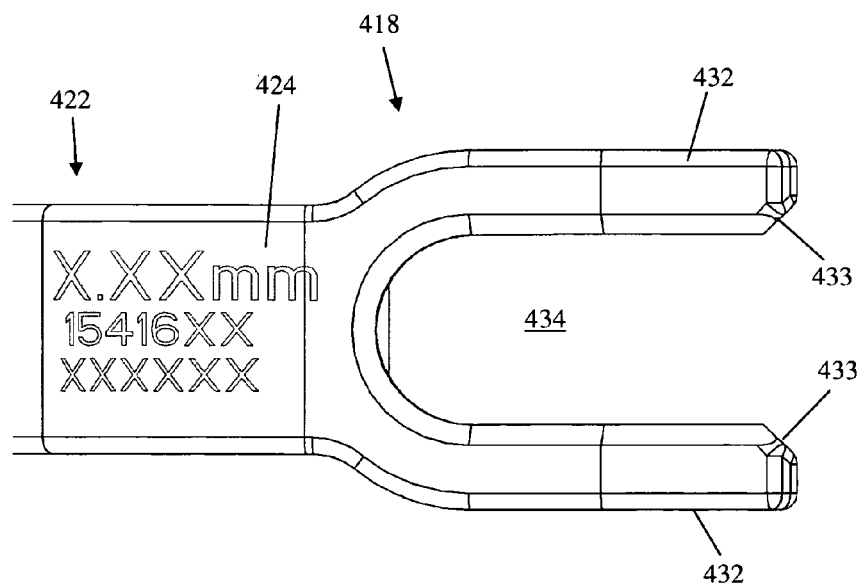
FIG. 27 is a top plan view of a first end of the bone plate of FIG. 23.

FIG. 22 illustrates a bone plate system 310 according to a fourth embodiment of the present invention. The bone plate system 310 is identical to the bone plate system 110 except that it is provided with a smaller size. Many different sizes of the bone plate system 110/310 may be provided without departing from the scope of the present invention.

Referring to FIGS. 23-27, an alternative example of a bone plate 412 is provided according to a fifth embodiment of the present invention. The bone plate 412 includes a first end 418, a second end 420, and a body portion 422 extending therebetween. The bone plate 412 further includes a first surface 424, second surface 426, and two lateral surfaces 428, 430 that form the perimeter of the bone plate 412. The first end 418 comprises a pair of first flanges 432 that extend from the body portion 422, and in effect are a continuation of the body portion 422 (as opposed to extending away from the body portion 22 at a particular angle). Unlike the first flanges 32 of the bone plate 12 described above, the first flanges 432 are not entirely planar. Instead, each of the first flanges 432 includes a curved portion 431 configured such that the first surface 424 has a concave curvature at the curved portion 431. The curved portions 431 increase the user friendliness of the bone plate 412 by enabling the first flanges 432 to be initially engaged with the first fixation element 14 from various angles of approach. The first flanges 432 define the sides of a slot 434 that is dimensioned to engage the first fixation element 14, as described above in relation to bone plate 12. The slot 434 is a generally U-shaped slot with its open end constituting a first terminal end of the bone plate 412. Each of the first flanges 432 includes a tapered portion 433 angling inward from the tip of the first flange 432 toward the slot 434. The tapered portions 433 facilitate initial engagement of the first flanges 432 with the first fixation element 14 by increasing the distance between the first flanges 432 at the mouth of the slot 434. The remaining features of the first end 418 of bone plate 412 are identical to the features of the first end 18 of the bone plate 12, and thus a repeat discussion is not necessary.

The second end 420 of the bone plate 412 includes a second flange 442 extending from the body portion 422. The body portion 22 is a generally elongated element that extends between the first end 418 and second end 420 of the bone plate 412. The body portion 422 includes a third flange 448 extending away from the second surface 426. These features are identical in form and function to the corresponding features of bone plate 12 described above, and further discussion is not necessary.

Figure 28:
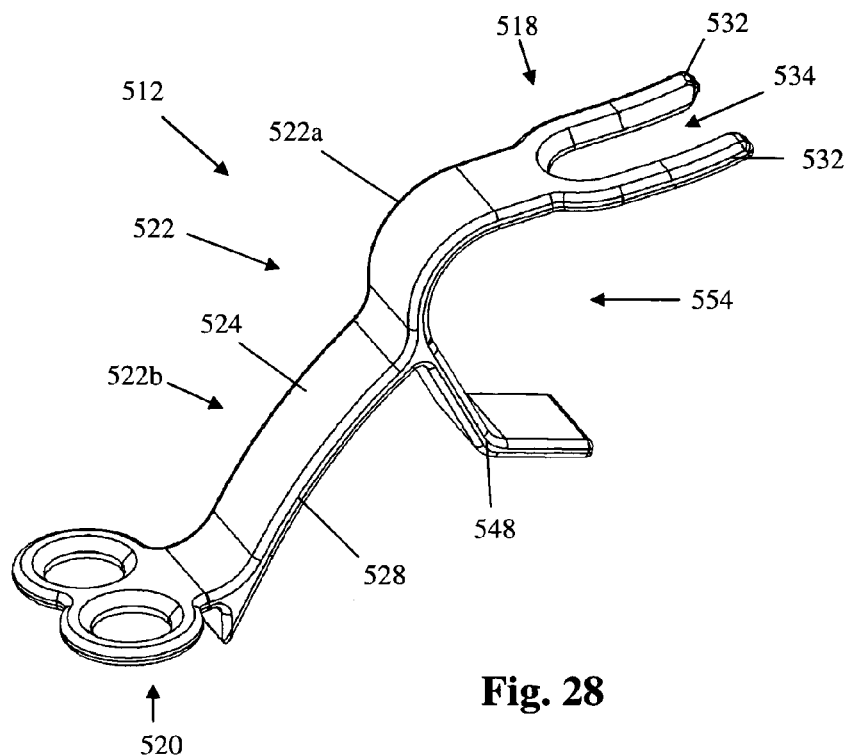
FIG. 28 is a perspective view of a bone plate forming part of a bone plate system configured for use during an open door laminoplasty procedure, according to a sixth embodiment of the present invention.
Figure 29:
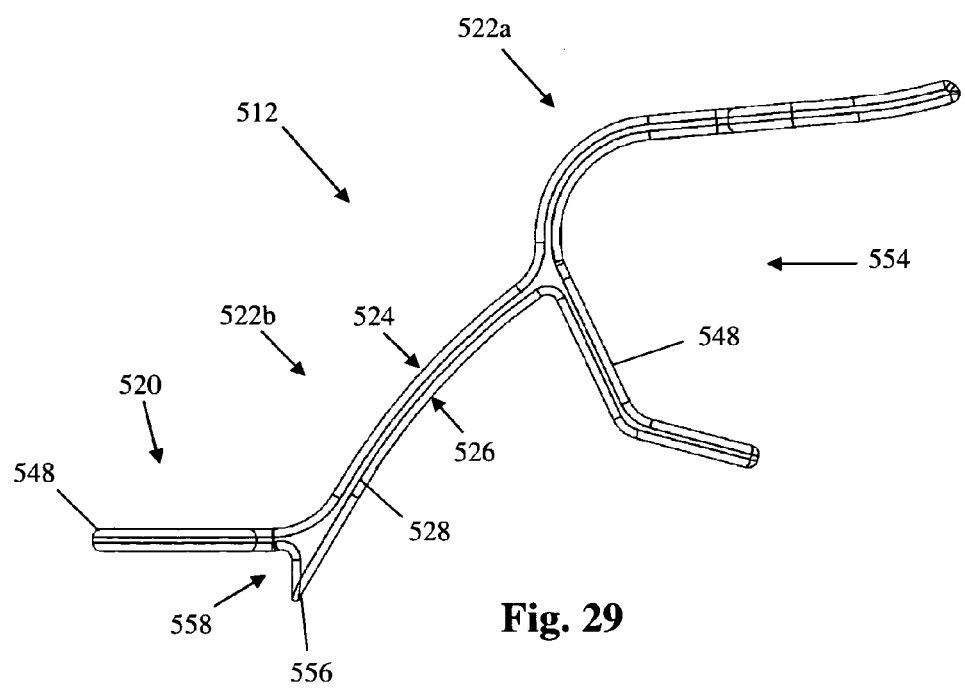
FIG. 29 is a side plan view of the bone plate of FIG. 28.
Figure 30:
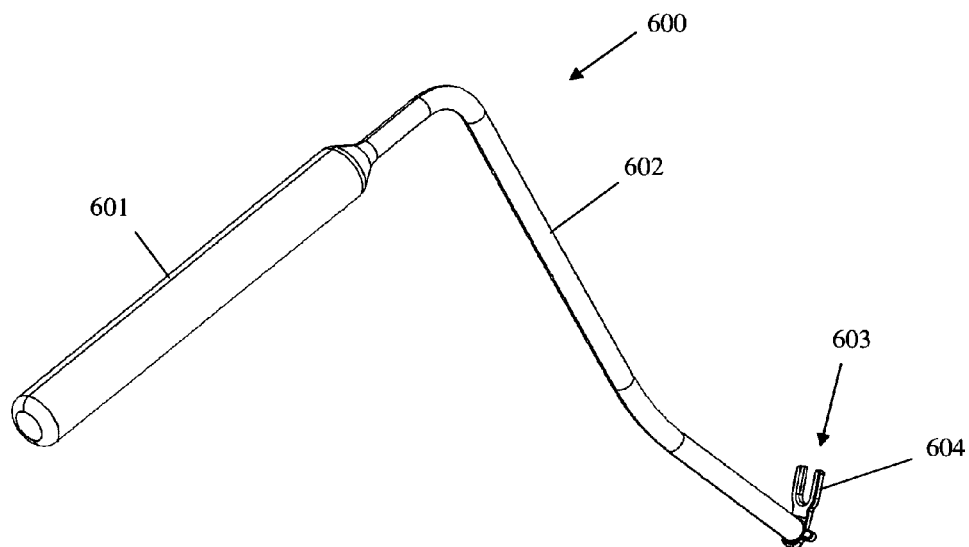
FIG. 30 is a perspective view of a template tool configured for use with a laminoplasty fixation system according to the present invention.
Figure 31:
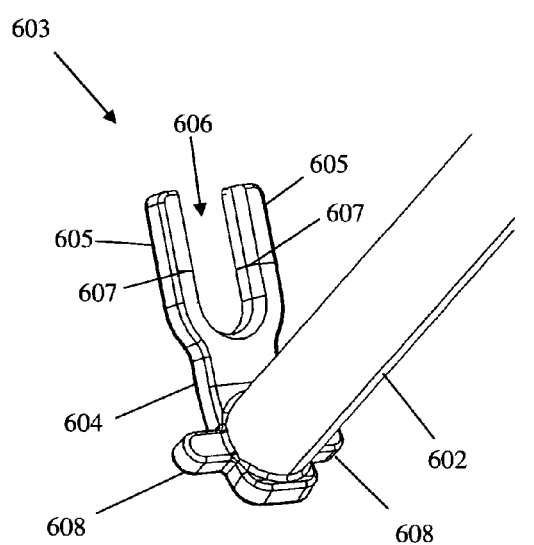
FIG. 31 is a perspective top view of a distal end of the template tool of FIG. 30.

Referring to FIGS. 28-29, an alternative example of a bone plate 512 is provided according to a sixth embodiment of the present invention. The bone plate 512 includes a first end 518, a second end 520, and a body portion 522 extending therebetween. The bone plate 512 further includes a first surface 524, second surface 526, and two lateral surfaces 528, 530 that form the perimeter of the bone plate 512. The first end 518 includes a pair of first flanges 532 and a U-shaped slot 534 formed therebetween. The second end 520 includes a second flange 542. The bone plate 512 is substantially similar to the bone plate 412 described above, in that the features of the first end 518 and second end 520 of the bone plate 512 are identical to the features of the first end 418 and second end 420 of the bone plate 412, rendering a repeat discussion of the details unnecessary. The difference between bone plate 512 and bone plate 412 resides in the features of the body portion 522.

The body portion 522 is a generally elongated element that extends between the first end 518 and second end 520 of the bone plate 512. The body portion 522 includes a third flange 548 extending away from the second surface 526. The third flange 548 is identical to and includes the corresponding features of the third flange 48 of the bone plate 12 described above. The body portion 522 further includes a first body portion 522a extending between the first end 518 and the third flange 548, and a second body portion 522b extending between the third flange 548 and the second end 520. The first and second body portions 522a and 522b have different radii of curvature such that the second body portion 522b has a more gradual curve than the first body portion 522a. The junction between the first body portion 522a and the third flange 548 forms a first crotch 554 that is configured for abutment against a first bony segment. The first crotch 554 of the bone plate 512 differs from the first crotch 54 of the bone plate 12 described above in that it is much larger. This feature of the bone plate 512 accommodates larger sized lamina bones, for example in patients who might have a larger bone size, or at spine levels that have a larger bone size (e.g. C7). At the second end 520 of the bone plate, the body portion 522 includes a terminal end 556 that extends beyond the junction of the second flange 542. The junction between the terminal end 556 and the second flange 542 forms a second crotch 558 that is configured for abutment against a second bony segment.

Referring to FIGS. 30-34, an example is provided of a template tool 600 configured for use with a laminoplasty fixation system 10 of the present invention. The template tool 600 includes a handle 601, a rod 602 and a distal end 603. The handle 601 is positioned at a proximal end of the template tool 600 and is configured to allow for user manipulation of the tool. The rod 602 is elongated and extends between the handle 601 and the distal end 603. The distal end 603 includes a foot 604. The foot 604 is used to help determine the appropriate size and positioning of the bone plate 12 and first fixation element 14 to be used during the laminoplasty procedure. The foot 604 may be provided as a removable attachment, or may be integrally formed with the template tool 600.

The foot 604 is shaped similarly to the first end 18 of the bone plate 12 of the present invention (or any of the other embodiments of the bone plates described herein. The foot includes a pair of flanges 605 and a U-shaped slot 606 positioned therebetween. The flanges 605 correspond in size and shape to the first flanges 32 of the bone plate 12. The slot 606 corresponds in size and shape to the slot 34 of the bone plate 12. In one embodiment, the foot 604 may include markings 607 (e.g. laser markings) on the flanges 605 to denote the proper positioning of the first fixation element 14. In the example shown, the foot 604 further includes a pair of lateral flanges 608 extending generally orthogonally from the foot 604 near the location where the foot 604 is joined to the rod 602.

Figure 33:
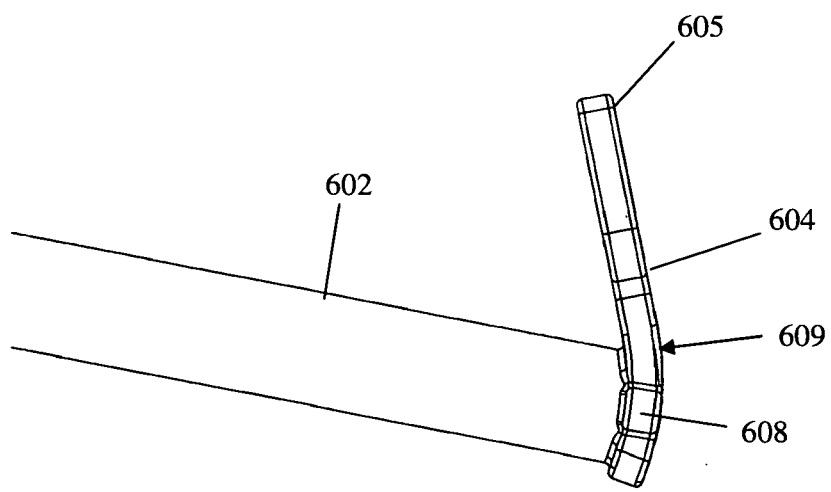
FIG. 33 is a perspective side view of a distal end of the template tool of FIG. 30.

FIG. 33 illustrates, by way of example and not by way of limitation, a general curvature of the foot 604. The foot 604 is shaped to accommodate the contours of the surgical site to provide optimized visibility for the surgeon. In the example shown in FIG. 30, the bottom surface 609 of the foot 604 has a generally convex curvature in order to accommodate the anatomical shape of the lamina and lateral mass of the target vertebra.

Figure 34:
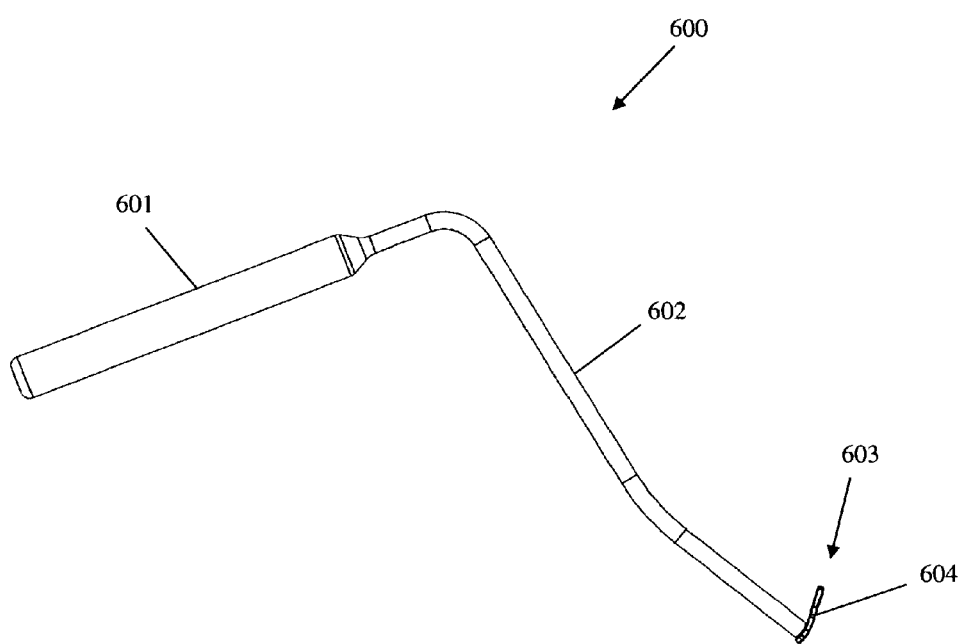
FIG. 34 is a side plan view of the template tool of FIG. 30.

As demonstrated by example in FIG. 34, the handle 601, rod 602 and attachment 604 are shaped to provide increased visibility of the operative site during use of the template tool 600. For example, the rod 602 includes two obtuse-angle bends, with the foot 604 extending away from the rod 602 and angled toward the rod 602 at the distal region of the foot 604. Various other configurations (e.g., number and degree of bends in rod 602 and/or general angle(s) of the foot 604) of the template tool 600 are possible without deviating from the scope of the present invention.

In use during a laminoplasty procedure involving the laminoplasty fixation system 10 described above, the surgeon would first identify the trough line and then gently mark it with a bovie or high-speed burr. The template tool 600 is then positioned such that the foot 604 is placed over the trough line. The lateral flanges 608 should be positioned to correspond to the trough line. This positioning of the lateral flanges 608 ensures that the U-shaped slot 606 is properly positioned over the lamina. A marking may be made using a bovie or high-speed burr in the lamina near the center of the U-shaped slot 606 (for example between the laser etchings 607). This marking will determine the entry point of the first fixation element 14 into the lamina. The template tool 600 can then be removed from the operative corridor and the hole for the first fixation element 14 may then be drilled into the lamina. The first fixation element 14 is then introduced into the laminar hole and advanced until the second surface 88 of the annular ledge 84 is flush with the bone. The procedure then proceeds as described above.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the invention is to cover all modifications, equivalents, and alternatives falling within the spirit and scope of the invention as defined herein.

What is claimed is:

1. A method for enlarging a spinal canal, comprising:
   inserting a first fixation element into a first lamina of a vertebrae;
   after inserting the first fixation element into the first lamina of the vertebrae, forming a trough through the first lamina of the vertebra adjacent to a first lateral mass to completely separate the first lamina from the lateral mass;
   forming a hinge groove into a second lamina of the vertebrae adjacent to a second lateral mass without separating the second lamina from the second lateral mass;
   coupling a first end of a bone plate to the first fixation element and the first lamina;
   lifting the first lamina away from the first lateral mass to create an enlarged configuration of the spinal canal;
   coupling a second end of the bone plate with a second fixation element to the first lateral mass to maintain the spinal canal in the enlarged configuration.

2. The method of claim 1, wherein the lamina is lifted using the bone plate.

3. The method of claim 1, wherein the lamina is lifted using a secondary instrument.

4. The method of claim 3, wherein the secondary instrument is a curette or a nerve hook.

5. The method of claim 1, further comprising determining proper placement of the first fixation element using a template tool.

6. The method of claim 1, wherein the first end of the bone plate comprises a pair of flanges defining a U-shaped slot.

7. The method of claim 1, wherein the bone plate is introduced to the first lamina at an oblique angle, then rotated into position such that the second end of the bone plate is adjacent to the first lateral mass.

* * * * *